United States Patent
Zapf (10) Patent No.: US 11,167,586 B2
(45) Date of Patent: Nov. 9, 2021

(54) RUNNING WHEEL

(71) Applicant: TRUMPF MEDIZIN SYSTEME GMBH + CO. KG, Saalfeld (DE)

(72) Inventor: Andreas Zapf, Leutenberg (DE)

(73) Assignee: TRUMPF MEDIZIN SYSTEME GMBH + CO. KG, Saalfeld (DE)

( * ) Notice: Subject to any disclaimer, the term of this patent is extended or adjusted under 35 U.S.C. 154(b) by 663 days.

(21) Appl. No.: 15/992,521

(22) Filed: May 30, 2018

(65) Prior Publication Data
US 2018/0361784 A1    Dec. 20, 2018

(30) Foreign Application Priority Data
Jun. 1, 2017   (DE) .......................... 102017209356.0

(51) Int. Cl.
| | | |
|---|---|---|
| *B60B 19/12* | (2006.01) | |
| *B60B 19/00* | (2006.01) | |
| *B60B 33/00* | (2006.01) | |
| *B60K 7/00* | (2006.01) | |
| *B62B 5/04* | (2006.01) | |

(Continued)

(52) U.S. Cl.
CPC .......... *B60B 19/125* (2013.01); *B60B 19/003* (2013.01); *B60B 33/0086* (2013.01); *B60K 7/0007* (2013.01); *B62B 5/04* (2013.01); *A61B 6/04* (2013.01); *A61G 7/08* (2013.01); *B60B 2200/242* (2013.01); *B60K 2007/0092* (2013.01); *B62B 2005/0471* (2013.01); *B62B 2301/02* (2013.01); *B62B 2301/25* (2013.01)

(58) Field of Classification Search
CPC ................ B60B 19/125; B60B 19/003; B60B 33/0086; B60B 2200/242; B60K 7/0007; B60K 2007/0092; B62B 5/04; B62B 2005/0471; B62B 2301/02; B62B 2301/25; A61B 6/04; A61G 7/08

USPC ........................................................ 301/5.23
See application file for complete search history.

(56) References Cited

U.S. PATENT DOCUMENTS 3,771,628 A *  11/1973  Close .................... B60B 33/021
                                                        188/189
10,406,854 B2    9/2019  Zhang et al.
(Continued)

FOREIGN PATENT DOCUMENTS

| CN | 105584290 | 5/2016 |
|---|---|---|
| DE | 822660 | 11/1951 |

(Continued)

OTHER PUBLICATIONS

Machine Translation of DE 102014115901 (Year: 2014).*
Extended European Search Report, European Application No. 18174770, completed Oct. 25, 2018, (6 pages).

*Primary Examiner* — James A Shriver, II
*Assistant Examiner* — Michael T. Walsh
(74) *Attorney, Agent, or Firm* — Barnes & Thornburg LLP (57) ABSTRACT

A running wheel for a patient positioning device (30) is provided. The running wheel has a wheel (1) and a receiving device (4) for rotatably receiving the wheel (1) around a first rotational axis (5), which is arranged centrally with respect to a circumference of the wheel (1). The wheel (1) has a wheel body (3), and multiple circumferential castors (7), each having a second rotational axis (8) arranged in a direction tangential to a circumference of the wheel (1), wherein the circumferential castors (7) form a bearing surface of the wheel (1).

19 Claims, 4 Drawing Sheets

(51) Int. Cl.
*A61B 6/04* (2006.01)
*A61G 7/08* (2006.01)

(56) References Cited

U.S. PATENT DOCUMENTS

| | | | |
|---|---|---|---|
| 2005/0134106 A1* | 2/2005 | Guile | B60B 1/00 |
| | | | 301/5.23 |
| 2006/0207838 A1* | 4/2006 | Kidd et al. | B60B 33/00 |
| | | | 188/12 |
| 2008/0018167 A1* | 1/2008 | Fuji | B60B 19/003 |
| | | | 301/5.23 |
| 2013/0025983 A1* | 1/2013 | Wolf | B60T 1/06 |
| | | | 188/72.4 |
| 2015/0167402 A1* | 6/2015 | Chang | E21B 47/09 |
| | | | 175/45 |
| 2018/0043951 A1 | 2/2018 | Uebelhart et al. | |

FOREIGN PATENT DOCUMENTS

| | | |
|---|---|---|
| DE | 102010051202 | 5/2012 |
| DE | 102014115901 A1 | 10/2014 |
| WO | WO2016/096437 | 6/2016 |

\* cited by examiner

RUNNING WHEEL

CROSS REFERENCES TO RELATED APPLICATION

This application claims the benefit of and priority to German Patent Application Serial No. 102017209356.0, filed on Jun. 1, 2017, which is incorporated herein by this reference in its entirety.

The invention relates to a running wheel, more particularly a running wheel for a patient positioning device.

Running wheels for patient positioning devices are referred to as castors, for example, which can be swiveled and locked around a vertical swivel axis.

If the castors are not locked around the vertical swivel axis and the castors can be swiveled freely, the patient positioning device, a hospital bed or operating table, for example, can easily be moved in all directions. This allows, for example, an operating table position in an operating theater to be easily approached and the operating table can be easily oriented.

However, if the patient positioning device is to be moved, more particularly by one person, over a longer distance, the patient positioning device is difficult to navigate if all castors are swiveling. It is advantageous if the swivel axis on at least one of the castors is locked. This is achieved by means of castors, the vertical swivel axis of which are lockable, or running wheels that cannot be swiveled around a vertical axis and which, if necessary, are moved downwards in order to make contact with a floor surface and hence act as a guide wheel.

However, such a lockable, swiveling bearing arrangement, which is easy to operate and easy to lock and release during operation, or a vertically movable bearing arrangement of the guide wheel is complex in terms of realization. Operation is likewise complex, since a guiding characteristic of the guide wheel has to be manually activated or deactivated by means of a blocking mechanism or a downward movement.

Therefore, the invention addresses the problem of providing a running wheel for easily implementing an arbitrary horizontal movement of a patient positioning device.

The problem is addressed by means of a running wheel according to the claims. Advantageous developments are the subject matter of the dependent claims.

According to one aspect of the invention, a running wheel for a patient positioning device contains a wheel and a receiving device for rotatably receiving the wheel around a first rotational axis, which is arranged centrally relative to a circumference of the wheel. The wheel has a wheel body and multiple circumferential castors, each having a second rotational axis, which are arranged in such a manner that each of the second rotational axes is arranged in a direction tangential to the circumference of the wheel, each of the circumferential castors forming at least sections of a bearing surface of the wheel.

This running wheel construction allows the patient positioning device to be moved both in a direction in which the wheel rotates around the first rotational axis, in order to move the patient positioning device in a longitudinal direction, for example, and also in a direction of the second rotational axis, in order to move the patient positioning device in a transverse direction, wherein the circumferential castors will then rotate. Consequently, the patient positioning device can be moved in a transverse direction without the wheel being pivoted around a vertical axis.

If, in the direction of the first rotational axis, preferably multiple circumferential castors are provided next to one another, the contact surface of the wheel will increase, thereby allowing the load capacity of the running wheel to be increased. At the same time, the pressure of the wheel on a floor covering decreases, thereby making the patient positioning device easier to move.

If the circumferential castors are preferably barrel-shaped, and the bearing surface therefore has an essentially constant circumferential line, the wheel will exhibit more uniform running behavior and hence largely prevent halting when the patient positioning device is being moved.

A preferred provision of a drive mechanism for driving the rotation of the wheel around the first rotational axis creates the possibility of moving the patient positioning device either autonomously via a remote control or manually with the help of the drive mechanism.

Preferably, the running wheel is provided with a further drive mechanism for driving a rotation of the circumferential castors. This creates the possibility of moving the patient positioning device either autonomously via a remote control or manually with the help of the drive mechanism.

A combination of the drive device for driving the rotation of the wheel and the drive device for driving the rotation of the circumferential castors allows the patient positioning device to be moved in any direction, autonomously or manually with the help of the drive mechanism.

If the running wheel preferably has a braking mechanism, by means of which a rotation of the circumferential castors around the second rotational axis can be braked or locked, the running wheel can act as a guide wheel and hence permit stable directional travel of the patient positioning device. The braking mechanism can be activated by manual actuation, in order to brake or lock the circumferential rollers. An actuation object is provided on the patient positioning device for this purpose. Alternatively, the braking mechanism can be activated automatically, wherein it is activated as the wheel rotates around its rotational axis, for example by means of a reciprocal effect with a housing not rotatable around the first rotational axis, or by centrifugal force.

A preferred construction of the braking mechanism having a brake disk rotatable around the first rotational axis allows the circumferential castors to be braked or locked by a brake element of the brake disk. As the wheel starts to rotate, the brake disk is first held unrotated with respect to a housing and rotated from an idle position to a locking position with respect to the wheel. In the idle position, the circumferential castors are freely rotatable, whereas in the locking position they are braked or locked. As the wheel continues to rotate, the brake disk then co-rotates with the wheel and remains in the locking position.

A normal force, generated by a preferably existing preload element, acting on the brake disk in the direction of a brake surface of a housing and also a rotation of the brake disk with respect to the housing cause a defined frictional force relative to the housing, and a defined braking or locking force is exerted on the circumferential rollers of the rotating wheel via the brake element of the brake disk.

Since, when the wheel starts to move due to a relative rotation of the brake disk with respect to the wheel, the brake disk rotates from the idle position to the locking position under the frictional force and, as the wheel continues to move, said brake disk continues to rotate into its locking position together with the wheel, the circumferential castors are automatically braked or locked and remain braked or locked, so that only a movement of the running wheel according to a rotational direction around the first axis is possible.

Preferably, the preload element provided applies a normal force to the brake disk in the direction of the housing. As a result, a defined frictional force for the brake disk relative to the housing is generated and a defined braking or locking force is exerted on the circumferential castors via the brake element of the brake disk.

The brake element can preferably be formed by protrusions. The protrusions can essentially protrude in the direction of the first rotational axis. At the same time, each of the circumferential castors is provided with at least one section, which encloses an angle to the respective rotational axis thereof of between 0° and 90° and the circumferential surface of which faces the protrusion, i.e. a section that is not cylindrical.

The protrusions of the brake element are arranged and designed in such a manner that, as the brake disk rotates relative to the wheel into the locking position, said protrusions come into contact with the sections, wherein the circumferential castors are braked or locked. The locking position of the brake disk with the protrusions cannot be defined by an exact angular relationship between the brake disk and the wheel. Instead, said locking position ensues from the position of the brake disk with respect to the wheel, in which position the protrusions of the braked brake disk are supported at the sections of the circumferential castors, thereby generating a frictional force between the protrusions and the sections, in order to brake or lock the circumferential castors.

If the angle between the sections and the second rotational axis is preferably a non-self-locking angle, the brake disk can be rotated back from the locking position to the idle position. This can be achieved, for example, by a slight backward rotation of the brake disk, through a movement of the patient positioning device, for example.

The protrusions can preferably be formed from pins which are fixed in the brake disk. This permits a simple construction.

Preferably, a brake lining can be provided between the brake disk and the housing. As a result, a defined frictional force can be better adjusted in connection with the preload elements and also, wear on the brake disk or the housing can be prevented or reduced and/or compensated.

Preferably, the braking mechanism has mass elements, which are mounted in such a manner that they move away from the first rotational axis under a centrifugal force as the wheel rotates around the first rotational axis. As a result of this movement, the circumferential castors can be automatically braked or locked as the wheel rotates around the first rotational axis.

Preferably, the patient positioning device is equipped with at least one of the aforementioned running wheels and is therefore, in case of a simple construction, easier to move.

If the running wheel is preferably mounted on the patient positioning device with respect to a vertical axis in a fixed manner, a bearing point around the vertical axis is not required. This simplifies the construction.

If the running wheel is mounted on the patient positioning device in a preferably vertically movable manner, it is possible for said running wheel to be used as a guide wheel when it is lowered to the floor. However, the guide wheel can also be moved vertically upwards, in which case, for example, only castors provided on the patient positioning device will be in use.

If the vertically movable running wheel preferably has a preload element via which said running wheel is moved downwards, contact with the floor is maintained and the patient positioning device can therefore also be steered over uneven floors or across thresholds.

According to one aspect of the invention, the patient positioning device can be moved in one direction in such a manner that the wheel body and the circumferential castors rotate around their respective rotational axes, or such that either only the circumferential castors (7) rotate or only the wheel body (3) rotates.

According to a further aspect of the invention, the patient positioning device is moved in such a manner that the wheel body of the running wheel rotates around the first rotational axis and the braking mechanism is activated such that the rotation of the circumferential castors around the second axes is locked.

Preferably, the braking mechanism is activated from the idle position into the locking position by a rotation of the brake disk caused by the frictional force with respect to the housing relative to the wheel.

Preferably, the protrusions on the brake disk are brought into contact with the sections of the circumferential castors as the wheel body rotates relative to the brake disk. As a result, the circumferential castors are locked, which in turn activates the braking mechanism.

The invention will now be explained using an embodiment making reference to the attached drawings.

In particular.

Figure 1:
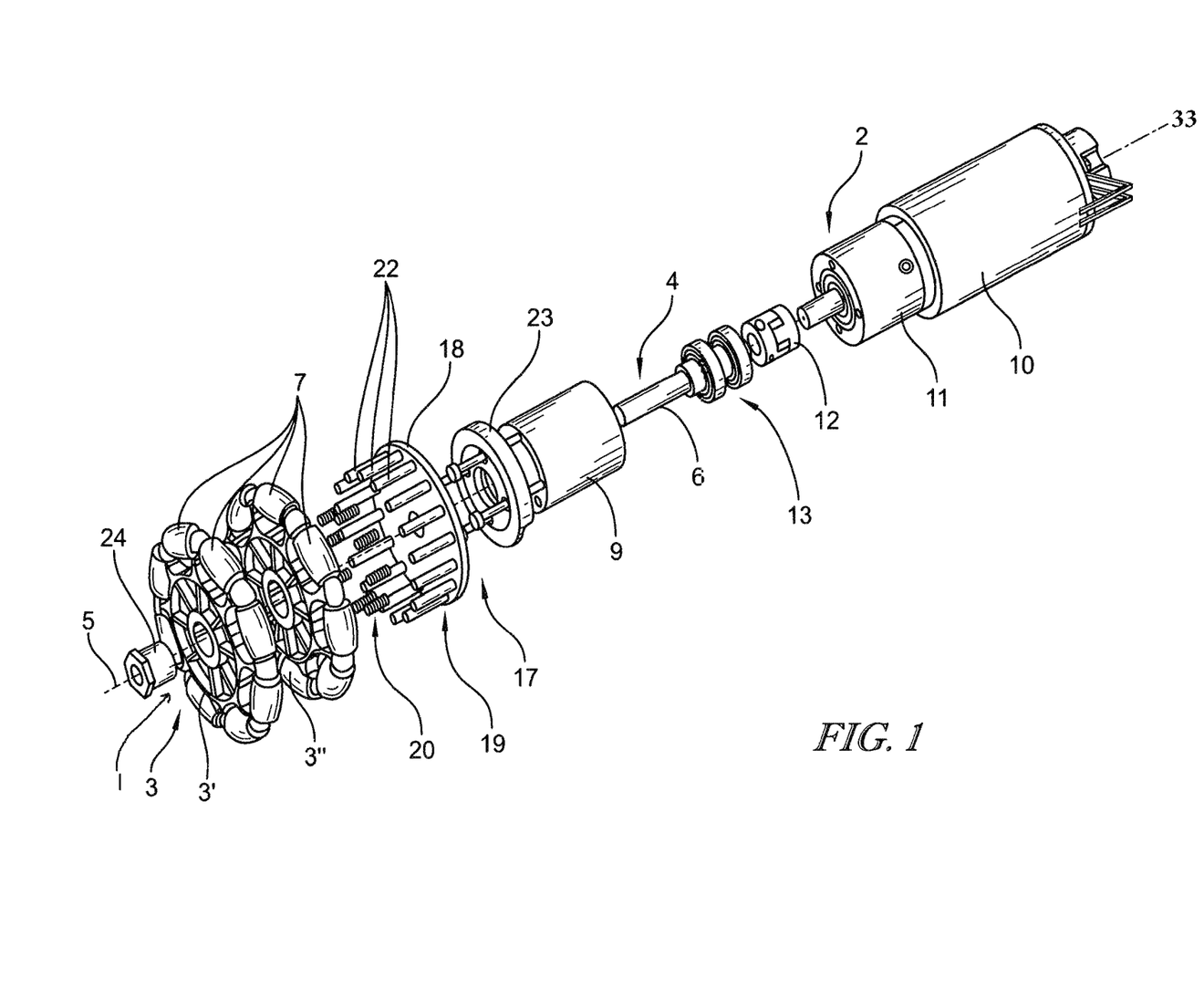
FIG. 1 shows an isometric exploded view of the running wheel according to the invention having an optional drive mechanism.
Figure 2:
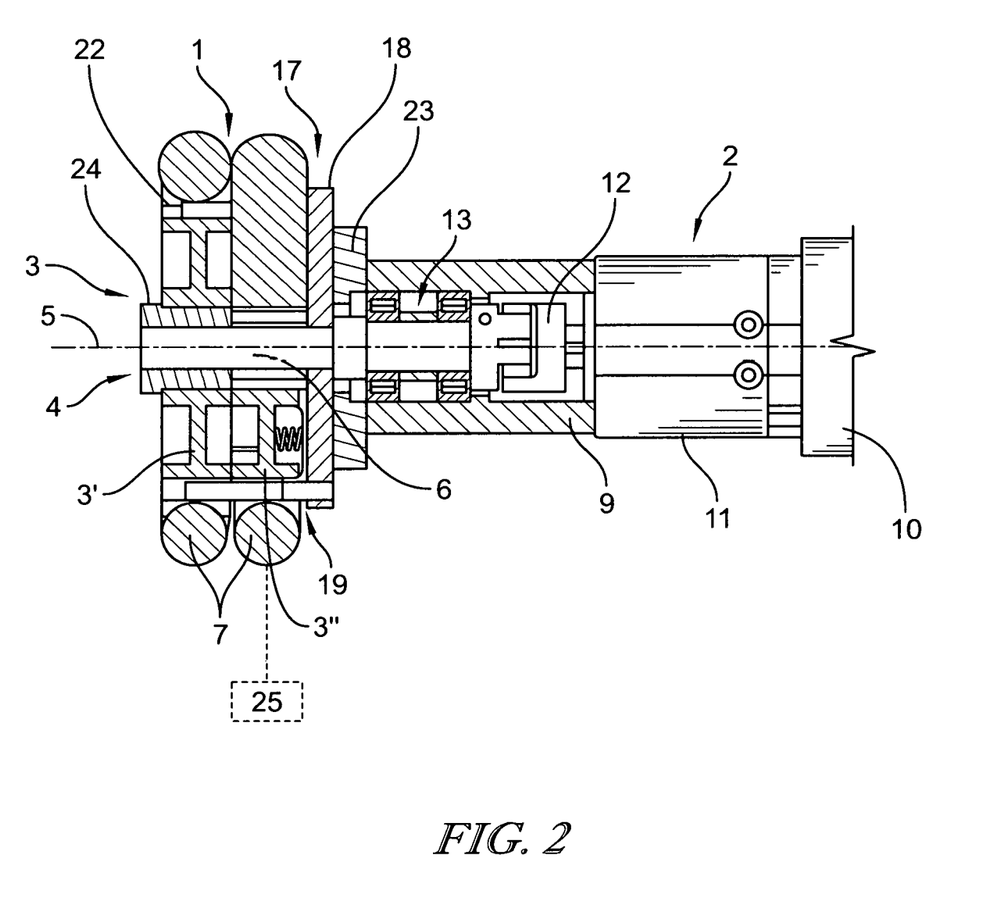
FIG. 2 shows a longitudinal section through the running wheel in FIG. 1 along a first rotational axis.

FIG. 1 shows an isometric exploded view of the running wheel according to the invention having a wheel 1 and an optional drive mechanism 2. FIG. 2 shows a longitudinal section cut along the axis 33 through the running wheel having the wheel 1 and the drive mechanism 2.

Wheel 1 has a wheel body 3. In this case, wheel body 3 is constructed from multiple parts 3', 3". Alternatively, however, it can also be formed from one part 3' or 3", wherein multiple wheel bodies can also be arranged next to one another.

In addition, the running wheel has a receiving device 4 for the rotatable receiving of the wheel 1 around a first rotational axis 5 arranged centrally with respect to a circumference of the wheel 1. In this case, the receiving device consists of a shaft 6, which is driven by the drive mechanism 2. The wheel body 3 is fixedly connected to the shaft 6 via a ledge in the shaft 6 and a shaft nut 24. Alternatively, the receiving device 4 can also be a non-driven pivot-mounted shaft. In a further embodiment, the shaft is fixedly mounted, and a bearing point is provided between the shaft and the wheel body.

The wheel 1 is provided with multiple circumferential castors. The circumferential castors are pivot mounted and each has a second rotational axis (FIG. 3) in a direction tangential to the wheel 1. The circumferential castors form a bearing surface of the wheel 1 and/or at least one part of the bearing surface each.

As shown in FIG. 1 and FIG. 2, multiple circumferential castors 7 are provided next to one another in multiple parts 3', 3" of the wheel body 3 in the direction of the first rotational axis 5. Alternatively, multiple circumferential castors 7 next to one another in only one part 3' or 3" of the wheel body 3 are also possible. In a further embodiment, only one circumferential castor 7 can also be provided in the direction of the first rotational axis 5.

The circumferential castors 7 are barrel-shaped, and therefore the bearing surface of the wheel 1 has a constant circumferential line, i.e. is "as round as possible". Alternatively, the circumferential castors 7 can also be designed cylindrical. A halting, which can occur if the wheel body rolls away, can be reduced or eliminated by a suitable choice of a soft material for the circumferential castors 7. A suitable, alternative embodiment of the wheel body 3 can further improve the running characteristics. For example, the wheel body 3 is able to bridge distances between the circumferential castors 7 along the circumferential line, thereby further supporting the approach of a constant circumferential line.

The receiving device 4 has a housing 9 and the drive mechanism 2 for driving a rotation of the wheel 1 around the first rotational axis 5.

The drive mechanism 2 contains an electric motor 10, a gear unit 11 and a shaft compensating coupling 12. The drive mechanism also comprises a bearing 13 for mounting the shaft 6.

Optimally, the running wheel is provided with a further drive mechanism 25 (FIG. 2) for driving a rotation of at least one of the circumferential castors 7, which is in contact with the floor. The drive means, drive motors for example, are integrated into the running wheels or, alternatively, provided separately from the running wheel and connected to the circumferential castors via force transmission devices.

The running wheel has a brake mechanism 17, which is designed to lock a rotation of the circumferential castors 7 around the second rotational axes 8.

The brake mechanism 17 has a brake disk 18, which is mounted to rotate around the first rotational axis 5 with respect to wheel body 3. The brake disk 18 is provided with a brake element 19. The brake element 19 is rotatable with respect to the wheel body 3, from an idle position in which the circumferential castors 7 can freely rotate, to a locking position in which the brake element 19 comes into locking contact with the circumferential castors 7. The brake element 19 is formed from protrusions 22, which protrude substantially from the brake disk 18 in the direction of the first rotational axis 5. Alternatively, the brake element 19 can also have a different form, for example, as an individual radial protrusion or as multiple radial protrusions which are arranged between the first rotational axis 5 and the circumferential castors in order to be in contact with sections of the circumferential castor, which are described later, for braking or locking. The protrusions 22 are formed from pins fixed in the brake disk. In alternative embodiments, however, they can also be provided in a different form, such as chamfers at the circumference of the brake disk 18. Crucially, the protrusions 22 come into braking or locking contact with the circumferential castors 7 when the brake disk 18 rotates towards the wheel body 3.

Where circumferential castors 7 are arranged adjacent in the direction of the rotational axis 5, the brake mechanism is able to brake or lock only one or more of said adjacent circumferential castors 7.

In addition, the running wheel contains a preload element 20, which applies a normal force, from the wheel body in the direction of the housing 9, onto the brake disk 18. In this case, the preload element 20 contains multiple spiral springs. Alternatively, the preload element 20 can also contain elastic blocks or plate springs, for example. The normal force causes the brake disk 18 to generate a frictional force with respect to the housing 9 as the brake disk 18 rotates with respect to the housing 9.

A brake lining 23 is provided between the brake disk 18 and the housing 9. In an alternative embodiment, the brake lining 23 can be omitted, and the brake disk 18 can rest directly on the housing, if a suitable material is chosen for the housing 9 and the brake disk 18.

In an alternative embodiment, the brake mechanism 17 is not provided with a brake disk for braking or locking the circumferential castors, but has instead a centrifugal brake 26 (FIG. 3), which is provided with mass elements that are arranged in such a manner that they move away from the first rotational axis 5 as the wheel 1 rotates around the first rotational axis 5. As a result of this movement, the mass elements act on the circumferential castors 7, either directly or via a brake mechanism, in order to lock the rotation of the circumferential castors 7 around the second rotational axes (8). In this case, the circumferential castors 7 are braked or locked via the protrusions. Alternatively, different brake elements can be used.

Figure 3:
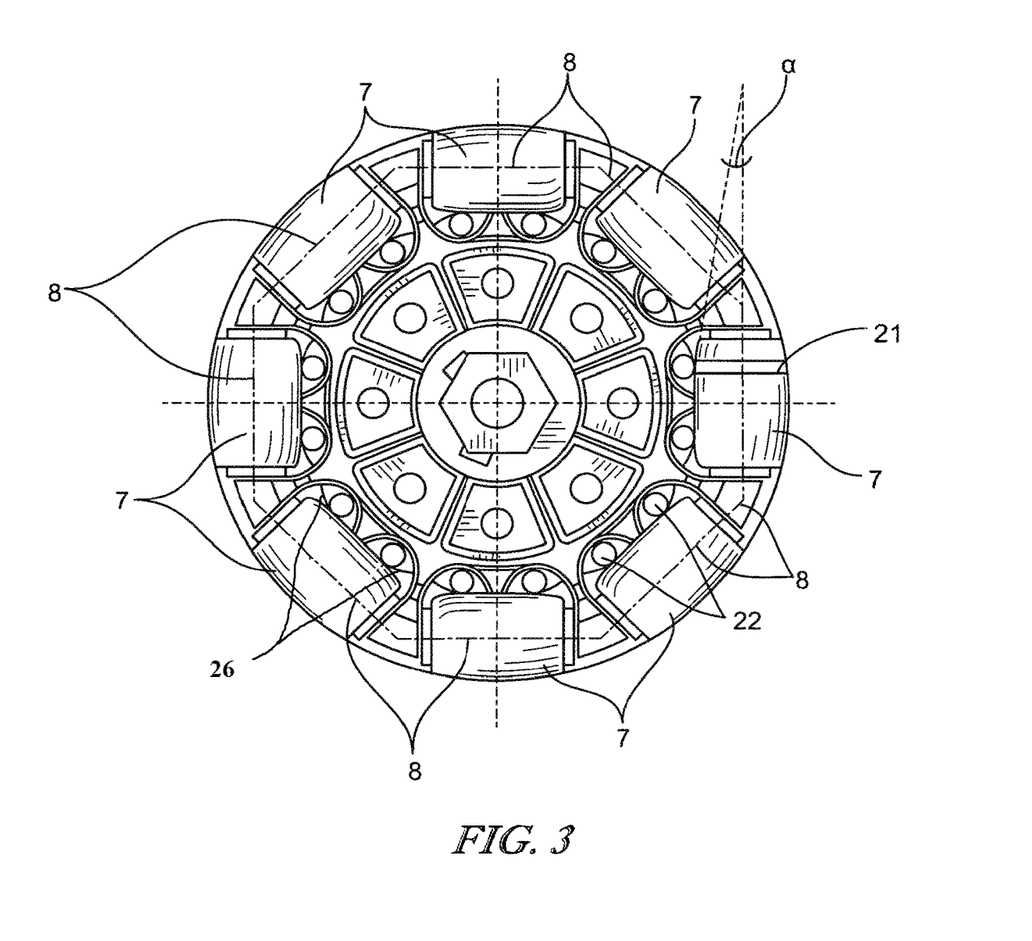
FIG. 3 shows a view of the running wheel in the direction of the first rotational axis.

FIG. 3 shows a view of the running wheel in the direction of the first rotational axis 5. As FIG. 3 shows, the circumferential castors 7 have sections 21 along their respective second rotational axis 8, said sections enclosing, together with their respective rotational axis 8, an angle $\alpha$, which is between 0° and 90°. Therefore, the sections are not cylindrical. Said sections 21, however, are not necessarily delimited sections. Instead, they can also be areas of a circumferential surface of the circumferential castors 7 along the rotational axis 8 thereof, without being delimited by an edge or similar. Likewise, the sections 21 do not need to form any even circumferential surfaces. Instead, they can be curved circumferential surfaces, wherein tangents at infinitesimal circumferential sections thereof enclose, together with the rotational axis 8, the angle $\alpha$, which is between 0° and 90°.

As the brake disk 18 rotates from the idle position to the locking position with respect to the wheel body 3, the protrusions 22 come into contact with the sections 21 in order to lock the circumferential castors 7.

The angle $\alpha$ is a non-self-locking angle, and therefore the brake disk can be rotated back from the locking position into the idle position. The angle $\alpha$ therefore depends on a surface of the circumferential castors 7 and the protrusions 22. In this case the angle $\alpha$ lies in a range from 5° to 10°, more particularly 6° to 7°. The locking of the circumferential castors 7 is released by a rotational movement of the wheel body 3 in an opposite direction. If the optional drive mechanism 2 is used, it can still rotate slightly in the opposite direction to that in which the driving of the wheel body 3 has ended, in order to release the lock.

Alternatively, the system can however also be designed sufficiently elastic for a restoring movement to occur automatically. Alternatively, or in addition, a "restore mechanism" via a spring or a comparable force application, can be provided. In this case, a restoring force is smaller than the frictional force required to achieve the locking position, in order to facilitate the locking process.

Figure 4:
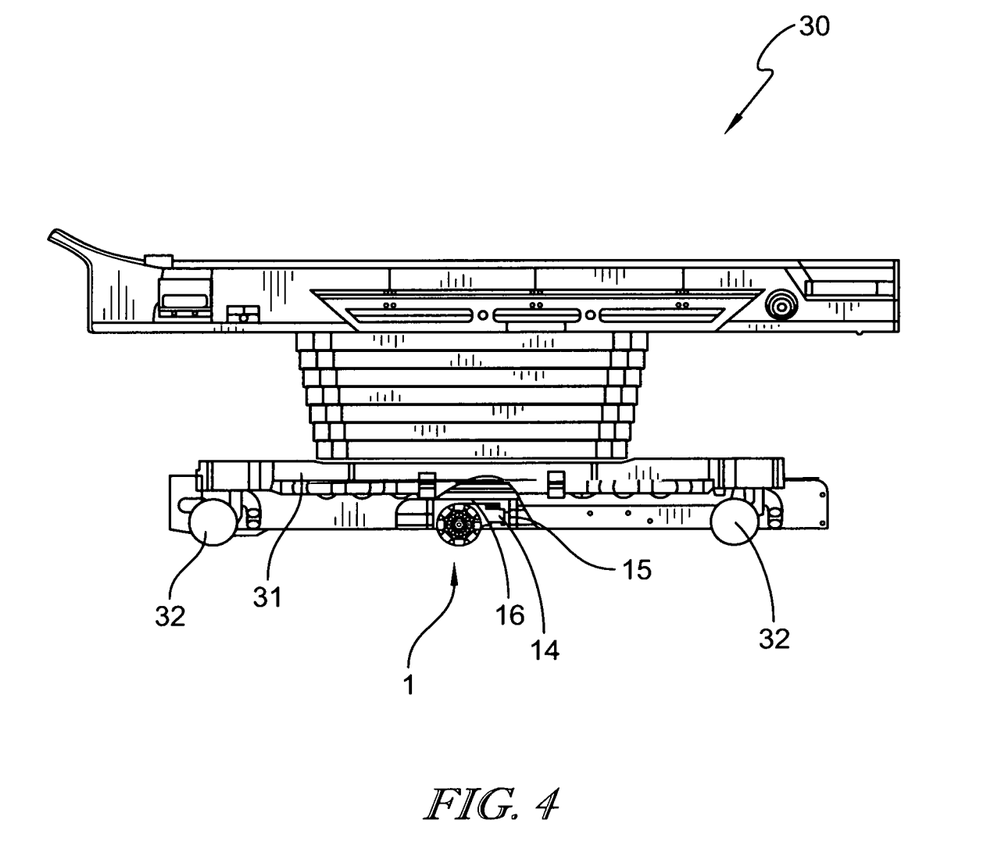
FIG. 4 shows a patient positioning device having a running wheel according to the invention.

FIG. 4 shows a patient positioning device 30 having the running wheel according to the invention. The patient positioning device 30 has castors 32 in the corner areas of a chassis 31. The running wheel is arranged centrally on the patient positioning device 30. Alternatively, the running wheel can also be provided instead of one of the castors 32 in the corner areas of the chassis 31, or the running wheels can be provided instead of two or more of the castors 32 in the corner areas. As a guide wheel in a vertical axis, the running wheel is fixedly mounted on the patient positioning device 30, and therefore the wheel 1 is unable to swivel around a vertical axis.

The receiving device 4 (FIGS. 1, 2) of the running wheel has a swivel arm 14, which is in turn provided with a swivel axis 15. Further, the receiving device 4 has a gas pressure spring as a preload element 16.

The running wheel is movably mounted on the patient positioning device 30 via the swivel arm 14. Further, the castor is pushed downwards by the gas pressure spring as the preload element 16. Alternatively, the running wheel can also be vertically movable via a different device, a linear guide, for example.

During operation, the patient positioning device 30 can be moved in any direction by means of running wheels according to the invention without the brake mechanism 17, and can likewise be rotated in any direction around a vertical axis. At the same time, both the wheel body 3 and the circumferential castors 7 are able to rotate around their respective rotational axes 5, 8.

If the brake mechanism 17 with the brake disk 18 is present, the wheel 1 rotates around the first rotational axis 5 as the patient positioning device 30 is moved in a predefined direction. At the same time, the brake disk 18 rotates, at the start of the movement, relative to the wheel 1, out of the idle position in which the circumferential castors 7 can freely rotate, and the sections 21 of the circumferential castors 7 come into contact with the protrusions 22 of the brake disk 18. As the wheel 1 continues to rotate, the brake disk 18 is co-rotated via the protrusions 22 that have come into contact with the circumferential castors 7, around the first rotational axis into the locking position. At the same time, the frictional force which is generated by the rotation of the brake disk 18 with respect to the housing 9 due to the normal force of the preload element 20, and which brakes the brake disk 18, causes a higher force of the protrusions 22 on the circumferential castors 7. As a result, the protrusions 22 push more firmly against the sections 21 of the circumferential castors 7, wherein these are braked or locked. If the patient positioning device 30 is moved further in the same direction, the brake disk 18 rotates with wheel 1 around the first rotary axis 5 and remains in the locking position under the frictional force. Consequently, the circumferential castors 7 remain locked and therefore the running wheel acts as a guide wheel. In an alternative brake mechanism embodiment, said brake mechanism is activated in a different form, via magnets for example.

If the patient positioning device 30 is moved slightly against the predefined direction, the wheel 1 moves in the opposite direction. The brake disk 18 is held by the frictional force (and because the angle α is a self-locking angle) and rotated relative to the castor body 3 into the idle position, in which the circumferential castors 7 can freely rotate. In an elastic embodiment of the system or if the restore mechanism is provided, the idle position is assumed autonomously. Consequently, the patient positioning device 30 can also be moved in a direction vertical to the running direction. In case of a further movement against the running direction, the brake disk 18 moves into a further locking position due to a section 21 inclined in the opposite direction.

All the features shown in the description, the claims below and the drawing may be essential to the invention either individually or in any combination if possible.

What is claimed is:

1. A running wheel, for a patient positioning device, having a wheel, and
   having a receiving device comprising a shaft for the rotatable receiving of the wheel around a first rotational axis, which is arranged centrally with respect to a circumference of the wheel, wherein
   the wheel has a wheel body, and multiple circumferential castors, each having a second rotational axis arranged in a direction tangential to a circumference of the wheel, wherein the circumferential castors are embodied in such a manner that they form the sections of a bearing surface of the wheel and the wheel body is connected to the shaft with a shaft nut,
   wherein the receiving device is provided with a drive mechanism for driving a rotation of the wheel around the first rotational axis, and wherein the running wheel is provided with a further drive mechanism for driving a rotation of at least one of the circumferential castors.

2. A running wheel according to claim 1, wherein multiple circumferential castors are provided next to one another in the direction of the first rotational axis.

3. A running wheel according to claim 1, wherein the circumferential castors are barrel-shaped.

4. A running wheel according to claim 1, wherein said running wheel has a brake mechanism, which is designed to lock a rotation of the circumferential castors around the second rotational axes.

5. A running wheel according to claim 4, wherein the receiving device has a housing, and the brake mechanism has a brake disk having a brake element,
   wherein the brake disk can be rotated around the first rotary axis with respect to the housing, the brake disk can be rotated from an idle position to a locking position with respect to the wheel body,
   wherein the braking element is designed to allow the circumferential castors to rotate freely in the idle position and to generate a locking contact with the circumferential castors in the locking position.

6. A running wheel according to claim 5, having a preload element which is designed to apply a normal force to the brake disk in the direction of the housing in order to cause the brake disk to generate a frictional force as the brake disk rotates with respect to the housing, the brake housing being designed to rotate from the idle position into the locking position when the frictional force is present by rotating the wheel body with respect to the brake disk and to rotate into the locking position with the wheel body.

7. A running wheel according to claim 5, wherein the brake element comprises protrusions which protrude from the brake disk parallel to the first rotational axis, and
   wherein the circumferential castors along the respective second rotational axis have at least one section which, together with the respective second axis, encloses an angle (α) of between 0° and 90° and the protrusions come into contact with the section as the brake disk rotates from the idle position into the locking position, in order to lock the circumferential castors.

8. A running wheel according to claim 7, wherein the angle (α) allows the brake disc to be rotated back from the locking position to the idle position.

9. A running wheel according to claim 7, wherein the protrusions are formed from pins fixed in the brake disk.

10. A running wheel according to claim 5, wherein a brake lining is provided between the brake disk and the housing.

11. A running wheel according to claim 4, wherein the brake mechanism has mass elements which are mounted in such a manner that they move away from the first rotational axis under a centrifugal force, as the wheel rotates around the first rotational axis, and are designed to lock the rotation of the circumferential castors around the second rotational axes by the movement of the mass elements.

12. A patient positioning device having a running wheel according to claim 5.

13. A patient positioning device according to claim 12, wherein the running wheel is fixedly mounted on the patient positioning device with respect to a vertical axis.

14. A patient positioning device according to claim 12, wherein the running wheel is mounted on the patient positioning device in a vertically movable manner.

15. A patient positioning device according to claim 14, having a preload element, which pushes the running wheel downwards.

16. A method for moving a patient positioning device according to claim 12, having a running wheel, said method comprising the following method step:
moving the patient positioning device in a direction, such that both the wheel bodies and the circumferential castors rotate around their respective rotational axes.

17. A method for moving a patient positioning device according to claim 12, having a running wheel, said method comprising the following steps:
moving the patient positioning device in a direction, such that the wheel rotates around the first rotational axis; and
activating the brake mechanism, such that the rotation of the circumferential castors around the second rotational axes is locked.

18. A method according to claim 16, having a running wheel, wherein the brake mechanism is activated as the wheel body rotates relative to the brake disk, under frictional force, from the idle position into the locking position.

19. A method according to claim 18, having a running wheel, wherein the brake mechanism is activated as the wheel body rotates relative to the brake disk and the protrusions come into contact with the sections.

* * * * *